United States Patent [19]

Cetrone

[11] Patent Number: 4,813,107

[45] Date of Patent: Mar. 21, 1989

[54] SPRING CLAMP

[75] Inventor: Vincent B. Cetrone, Warren, Ohio

[73] Assignee: Warren Tool Corporation, Hiram, Ohio

[21] Appl. No.: 92,897

[22] Filed: Sep. 4, 1987

[51] Int. Cl.4 ............................................. A44B 21/00
[52] U.S. Cl. ....................................... 24/557; 24/486; 24/489
[58] Field of Search ................. 24/486, 557, 562, 564, 24/489, 506, 511, DIG. 29

[56] References Cited

U.S. PATENT DOCUMENTS

| 2,525,985 | 10/1950 | Weymouth | 24/511 |
| 2,591,477 | 4/1952 | Tegarty | 24/557 |
| 2,885,758 | 5/1959 | Russo et al. | 24/562 |
| 3,341,909 | 9/1967 | Havener | 24/486 |
| 3,348,275 | 10/1967 | Lawrence | 24/DIG. 29 |
| 3,579,751 | 5/1971 | Jonckheere | 24/557 |
| 3,934,316 | 1/1976 | Driscoll | 24/486 |
| 4,071,930 | 2/1978 | Tanaka | 24/252 R |
| 4,079,765 | 3/1978 | Hatayan | 145/46 |
| 4,145,793 | 3/1979 | Berlet | 24/137 A |
| 4,192,441 | 3/1980 | Batts | 223/96 |
| 4,277,864 | 7/1981 | Orson, Sr. | 24/557 |
| 4,312,089 | 1/1982 | Taylor | 9/8 R |
| 4,395,799 | 8/1983 | Batts | 24/557 |
| 4,506,416 | 3/1985 | Ohminato et al. | 24/67 R |
| 4,514,885 | 5/1985 | Delahousse et al. | 24/489 |
| 4,616,113 | 10/1986 | Jank et al. | 24/562 |

FOREIGN PATENT DOCUMENTS

| 1391713 | 2/1965 | France | 24/486 |
| 0398487 | 3/1966 | Switzerland | 24/557 |
| 0796846 | 6/1958 | United Kingdom | 24/557 |

Primary Examiner—Victor N. Sakran
Attorney, Agent, or Firm—Renner, Kenner, Greive, Bobak, Taylor & Weber

[57] ABSTRACT

A non-metallic spring clamp (10). The spring clamp (10) includes a first body member (13) having a jaw end (20) and a handle end (21), and a second body member (14) having a jaw end (20) and a handle end (21). A bridging member (15) is integral with the first body member (13) and second body member (14), and is interposed between the jaw end (20) and handle end (21) of each. A spring (12) is interposed between the respective handle ends (21) so as to engage each handle end (21). Means (27) are provided to retain the spring (12) in engagement with each handle end (21). Means (26), likewise, are provided to laterally support the spring (12) on each handle end (21).

15 Claims, 3 Drawing Sheets

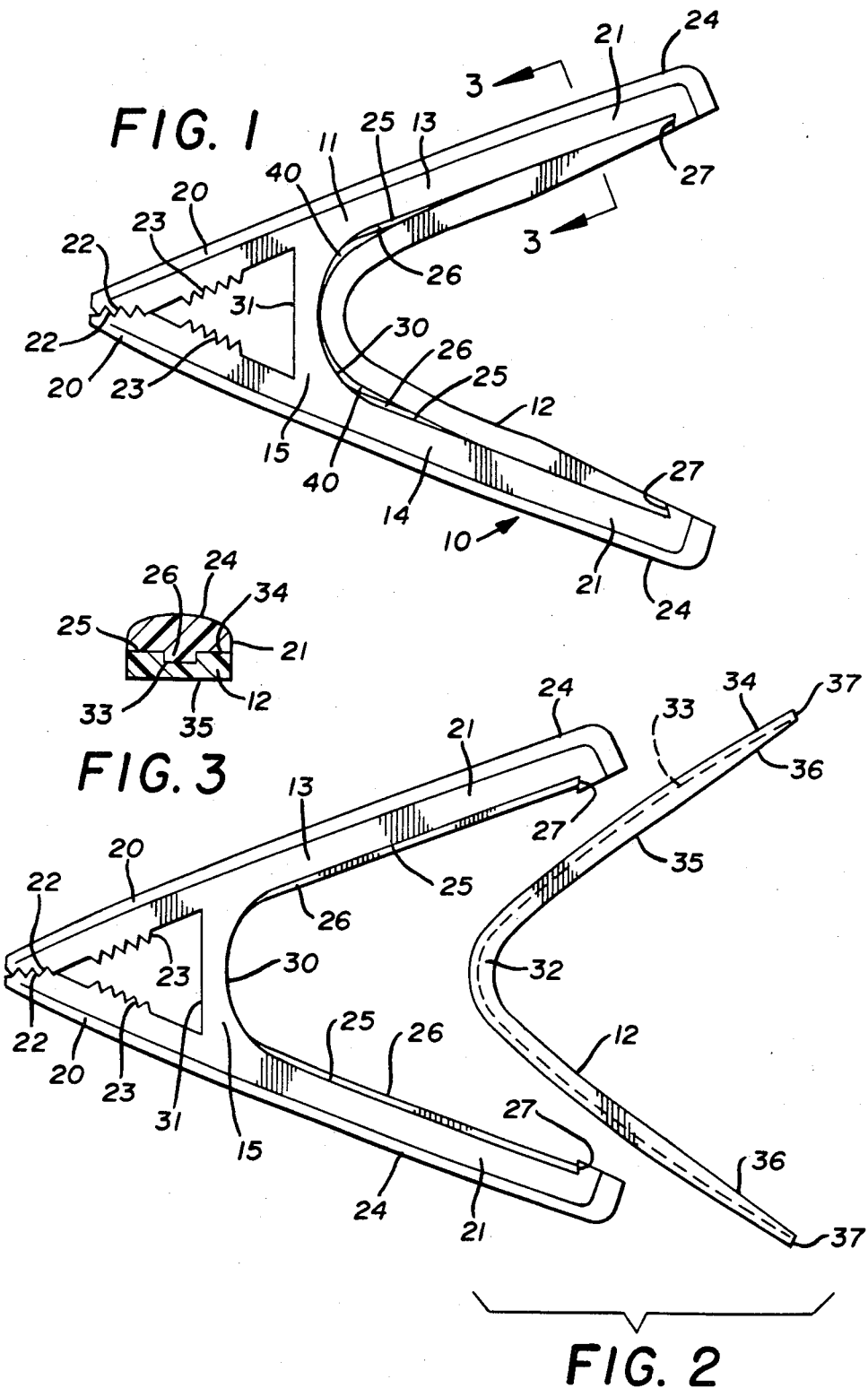

SPRING CLAMP

TECHNICAL FIELD

The present invention relates generally to clamps. More particularly, the present invention relates to spring clamps. Specifically, the present invention relates to a non-metallic spring clamp having a one-piece body with an interchangeable, non-metallic spring member.

BACKGROUND ART

Spring clamps have been known in the tool industry for quite some time. Spring clamps, of the type to which the present invention is directed, generally are of a plier-like configuration. These clamps are made of multiple stamped metal parts and have a gripping end and handle end with a hinge pin therebetween. The hinge pin acts not only as a fulcrum but also serves to pivotally join together the individual parts of the clamp. A metal spring, usually a torsional helical spring or leaf spring, is secured within the handle end, in cooperation with the hinge pin, to generate the clamping force of the spring. A typical spring clamp of this type is the HARGRAVE ® Spring Clamp manufactured by Warren Tool Corporation, Hiram, Ohio (HARGRAVE is a registered trademark of Warren Tool Corporation.)

These known spring clamps suffer from several inherent problems. To begin with, being made of metal such as steel, the clamps are subject to corrosion in the typical work environment. Furthermore, the multiple piece assembly requires considerable man-hours to assemble the clamp, thereby significantly increasing the cost of the article. Also the relatively thin metal clamp is likely to be permanently, albeit accidentally, deformed in use if it is stepped upon, struck or dropped.

The metal spring clamp is limited in its usage. For example, the metal clamp is not usable with wood, or similar materials, which can be marred by the metal jaws. It is necessary to install suitable jaw inserts or pads on the metal clamps to use them with such material. The metal clamps are not usable with electrical or electronic components as they cause a hazardous risk in shorting the components and shocking the user. Also, the metal clamps are not usable in sterile environments, such as surgical operating rooms and medical laboratories, because they are not easily sterilized. Even if they are sterilized, the metal to metal contact of the clamp parts wear and cause metal deposits to contaminate the otherwise sterile environment.

Efforts to make non-metallic spring clamps have been unsuccessful; and generally have resulted in small clips which do not possess sufficient clamping force to function in the same manner as metal spring clamps. These clips generate merely clamping forces great enough to allow the clip to be attached to an article, such as clips used for identification badges which attach to a person's clothing.

Despite the inherent problems and limitations of prior art spring clamps, and the need for a usable non-metallic spring clamp, none has yet been developed which provides an inexpensive simple construction capable of producing clamping forces equivalent to the clamping forces of metal spring clamps.

DISCLOSURE OF THE INVENTION

It is, therefore, an object of the present invention to provide a non-metallic spring clamp of simple configuration.

It is another object of the present invention to provide a non-metallic spring clamp, as above, capable of producing clamping forces equivalent to metal spring clamps.

It is a further object of the present invention to provide a non-metallic spring clamp, as above, having interchangeable non-metallic springs.

It is yet another object of the present invention to provide a non-metallic spring clamp, as above, having jaws suitable for engaging articles having a variety of different configurations.

It is still a further object of the present invention to provide a non-metallic spring clamp, as above, having jaws that are less likely to mar surfaces, so as to eliminate the need for jaw inserts or pads.

It is still a further object of the present invention to provide a non-metallic spring clamp, as above, that can be sterilized and used in a sterilized environment.

These and other objects of the present invention, as well as the advantages thereof over existing and prior art forms, which will be apparent in view of the following specification, are accomplished by means hereinafter described and claimed.

In general, a spring clamp, according to the concept of the present invention includes a first body member and a second body member each having a jaw end and a handle end. A bridging member is integral with the body members and is interposed between the jaw end and the handle end of each. A spring is interposed between the respective handle, ends, and retained in engagement with each handle end. Means are provided to laterally support the spring on each handle end.

BRIEF DESCRIPTION OF THE DRAWINGS

FIG. 1 a side elevational view of a spring clamp embodying the concept of the present invention.

FIG. 2 is an exploded side elevational view of the spring clamp depicted in FIG. 1.

FIG. 3 is a fragmentary cross-sectional view taken substantially along line 3—3 of FIG. 1.

EXEMPLARY EMBODIMENTS FOR CARRYING OUT THE INVENTION

Figure 5:
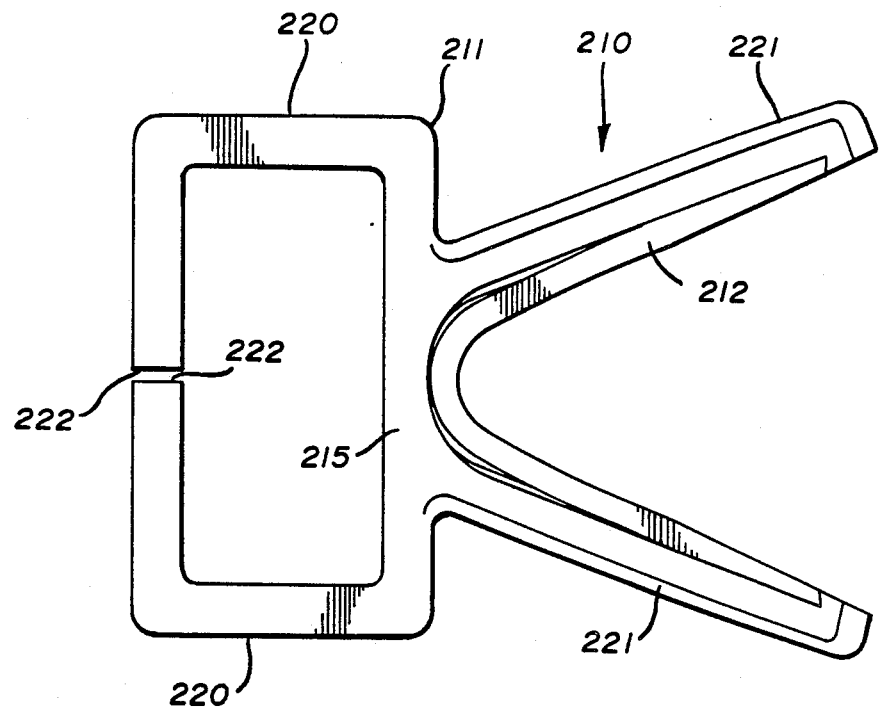
FIG. 5 is a side elevational view of an alternative configuration for a spring clamp embodying the concept of the present invention.

A spring clamp, according to the concept of the present invention, is indicated generally by the numeral 10 in FIG. 1, of the accompanying drawings. The spring clamp 10 comprises a unitary body 11 and a spring 12.

Before delving into the structural features of the spring clamp 10, it should be noted that, as a feature of the present invention, the spring clamp 10 preferably is made of a non-metallic material having suitable mechanical qualities. Preferably, the material may be a moldable material having a good strength to weight ratio, and which is substantially rigid yet flexible, with sufficient memory to return to its original molded shape. A material which exhibits these desirable qualities in nylon, although many other materials exist which are equally acceptable and, therefore, are contemplated within this disclosure. Also, it may be desirable to construct the spring clamp 10 from a composite of materials, with certain parts of the spring clamp 10 being made of one material—having high strength albeit non flexible—and other parts made of another material—having greater flexibility but with less strength. Similarly, part or all of the spring clamp 10 may be constructed of a metal or metal/non-metal composite material, provided the aforesaid mechanical qualities are considered.

An additional consideration in selecting the material from which the spring clamp 10 is constructed is the ability of the material to be sterilized using known sterilizing techniques. Therefore, the material should be capable of withstanding the elevated temperatures of an autoclave; or alternatively the material should be stable under exposure to sterilizing radiation.

Body 11 includes a first body member 13 and a second body member 14 joined together by an integral bridging member 15. Each body member includes a jaw end 20 and handle end 21, and are so oriented relative to each other such that, in a free state, jaw ends 20 are adjacent each other while handle ends 21 are farthest apart from each other. If body 11 is made of a moldable material, it is preferred that body 11 be molded in this free state, as depicted in FIG. 2.

Each jaw end 20 has a first set of teeth 22 located at the distal end and a second set of teeth 23 located inwardly of teeth 22. As it can be appreciated, jaw end 20 is capable of gripping a variety of articles of different shapes and sizes. Smaller articles may be gripped by teeth 22 while larger articles may be gripped by teeth 23.

Each handle end 21 is configured to present a smooth, contoured outward surface 24 which may be comfortably gripped by a user. For ease of manufacture, the contoured shape of outward surface 24 may extend along the full length of the respective body member, from handle end 21 to jaw end 20. Conversely, jaw end 20 may be configured differently from handle end 21 as would be appreciated by one skilled in the art.

Each handle end 21 further includes an inward surface 25 extending substantially the full length of handle end 21. Inward surface 25 is a substantially planar surface having a central longitudinal rib 26 extending along the full length thereof. At the distal end of handle 21, inward surface 25 terminates with a convergingly inclined retaining wall 27 extending transversely along the full width of handle 21. Rib 26 and retaining wall 27 serve to orient and secure spring 12 to body 11, as will become apparent hereinbelow.

The interior end of inward surface 25 merges into the arcuate wall 30 of bridging member 15, as depicted in FIG. 2. Arcuate wall 30 defines a radius sufficiently large enough to permit flexure of bridging member without concentration of stress at any given point. Accordingly, the radius of arcuate wall 30 may vary depending upon the type of material used for bridging member 15, the size and thickness of bridging member 15, and the size and material of spring 12, as will be appreciated by one skilled in the art after considering the disclosure herein.

Opposite arcuate wall 30, bridging member 15 has a substantially planar wall 31, which planar wall 31 is adjacent to, and defines the innermost extreme of, the jaw region of the spring clamp 10. Again, depending upon the material and size of bridging member 15, it may be desirable to configure wall 31 to be other than planar. It may, for example, be desirable to configure wall 31 either to be parallel or symetrical to arcuate wall 30.

As may be appreciated body 11, as thus configured from an appropriate material, may be suitable as a spring clamp. Indeed, using a material of sufficient resiliency and memory, particularly for bridging member 15, sufficient clamping force may be achieved, thereby obviating the need for spring 12. However, if additional spring force is required, or if it is desirable to change the spring force to meet specific requirements, spring 12 may be employed, as depicted in FIG. 1.

Spring 12 is made of a resilient flexible material, which may be a metallic, semi-metallic, or non-metallic material. Likewise, it may be of the same material as body 12. Depending upon the material used, spring 12 may be molded, stamped or otherwise worked into the desired configuration.

The configuration of the worked spring 12 is substantially rectangular in cross-section, as depicted in FIG. 3, having a width approximately equal to the width of handles 21. The spring is folded about its longitudinal mid-line forming a rounded bend 32 as depicted in FIG. 2. A longitudinal groove 33 extends fully along the outer surface 34 of spring 12. The inner surface 35 of spring may be substantially planar or it may be suitably configured—for example it may be rounded. Furthermore, inner surface 35 preferably is tapered 36 slightly toward the ends of spring 12 so as to permit greater movement of handles 21 when spring 12 is installed in body 11, as will become apparent hereinbelow. The distal end walls 37 are angled complementary to retaining walls 27 of handles 21 to permit secure engagement therewith.

When spring 12 is positioned onto body 11, it is located interiorly of handles 21. Groove 33 engages rib 26 to laterally position and secure spring 12 to body 11. When fully received between handles 21, end walls 37 engage retaining walls 27, respectively. Because of the angle of each, end walls 37 will be urged tightly into engagement with retaining walls 37 when handles 21 are squeezed together, thereby preventing spring 12 from disengaging handle 21.

When spring 12 is secured to body 11, the innermost region of bend 32 contacts arcuate wall 30 about the midpoint thereof when the clamp 10 is in an unflexed condition. As depicted in FIG. 1, spaces 40 are provided between spring 12 and arcuate wall 30 or handles 21 when the clamp 10 is unflexed. These spaces 40 provide clearance for displacement of spring 12 when handles 21 are manipulated. Such clearance avoides binding of spring 12 resulting in excessive stress which may damage spring 12, body 11, or both. Furthermore, as the clamp 10 is flexed, spring 12 displaces into spaces 40, extending the length of bend 32 and, thereby, amplifying the force of Spring 12 on body 11 without generating excessive stresses within spring 12.

It should be appreciated that body 11 can be used with different springs 12 to produce different clamping forces. Manufacturing is thus economized because one body style can be made and fitted with different spring sizes to produce different clamp. Likewise, it may be desirable for the user to have several springs which can then be interchanged with the body to provide a clamping force suitable for the particular application.

Figure 4:
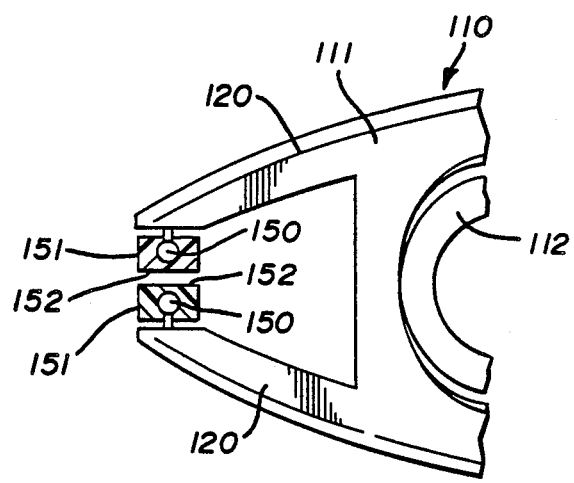
FIG. 4 is an enlarged fragmentary elevational view, partially in cross section, of an alternative jaw configuration of the spring clamp depicted in FIG. 1.

The foregoing advantages and characteristics, while described in conjunction with a preferred embodiment, are likewise associated with at least three alternative embodiments. A first alternative embodiment, depicted in FIG. 4, as spring clamp 110. The body 11 and the spring 112 of the spring clamp 110 is essentially identical to body 11 and spring 12 of the spring clamp 10. Accordingly, only the jaw end 120 of the spring clamp 110 is depicted to permit discussion of the modification embodied therein.

Specifically, each jaw end 120 has a suitably configured ball stud 150 onto which is movably secured a jaw pad 151. Jaw pad 151 may have a mating socket, for example, which clips onto ball stud 150. Such an arrangement permits pad 151 to pivot slightly relative to jaw end 120, thereby permitting the face 152 of each pad 151 to squarely grip the work piece.

It should be appreciated that other configurations of jaw end 120 can be employed to permit the pivotal mounting of pads 151 and such other configurations are contemplated herein. Also it should be appreciated that pads 151 can be made from a variety of materials, different than the material from which body 11 is constructed. Depending upon the use, pads 151 may be constructed of a metal, a plastic, or a soft, non-marring rubber or the like. Likewise, as with spring 112, a variety of pads 151 may be provided, permitting the user to select the appropriate set of pads to meet the requirements of the application.

Another alternative embodiment of a spring clamp 210 is depicted in FIG. 5. Again, the modification in this embodiment is found in the jaw ends 220 of the body 211, with the handles 221 and the spring 212 being substantially identical to those previously discussed hereinabove.

In the spring clamp 210, jaw ends 220 extend outwardly from the vicinity of the bridging member 215 to form a deep-reaching C-shaped jaw configuration. Jaw ends 220 each terminate in a jaw face 222 which, although depicted as being substantially planar in FIG. 5, may have teeth as hereinabove discussed with respect to the spring clamp 10. The configuration of the spring clamp 210 renders it suitable for gripping material having a flange or similar member along its edge. The deep throat of jaw ends 220 pass over the flange thereby enabling jaw face 222 to grip the work piece interiorly of the flange.

Figure 6:
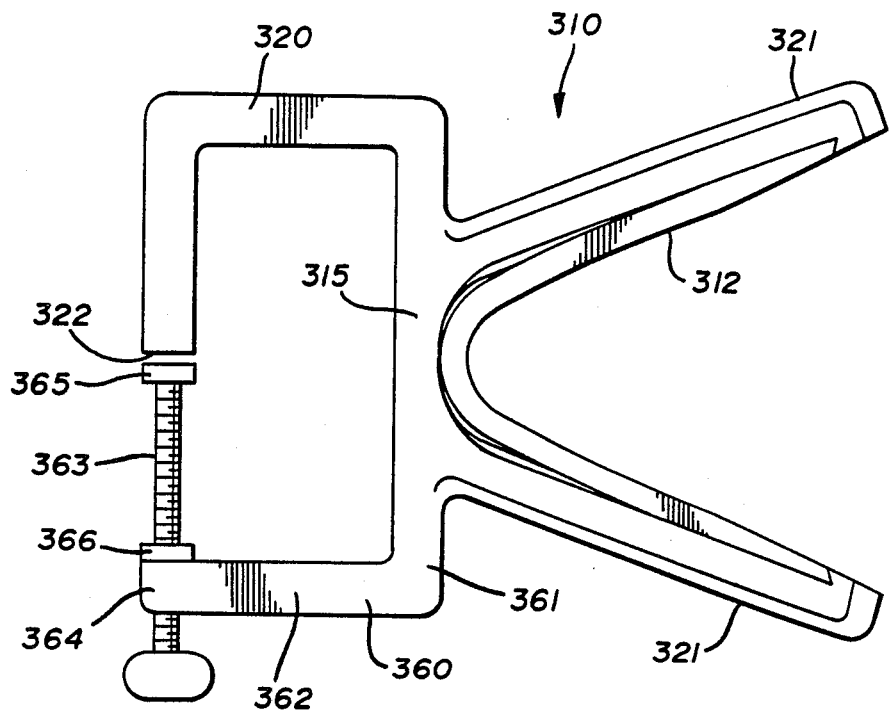
FIG. 6 is a side elevational view of another alternative configuration for a spring clamp embodying the concept of the present invention.

A variation of this embodiment is depicted in FIG. 6, wherein the spring clamp 30 provides for an adjustable opening in the jaws. The spring 312, handle ends 321 and bridging member 315 are identical to those elements of the spring clamp 210 depicted in FIG. 5. So, too, is one of the jaw ends 320 of the body 311. The opposing jaw end 360 incorporates the modification of this embodiment.

Opposing jaw end 360 includes a lateral arm 361 extending from bridging member 315; and a longitudinal arm 362 extending from the lateral arm 361. An adjustable thumb screw 363 threadably engages the distal end 364 of longitudinal arm 362 so as to be adjustable relative thereto. A pad 365 is carried on the end of thumb screw 363 in opposition to the jaw face 322 of jaw end 320. By manipulation of thumb screw 363, the spacing between jaw face 322 and pad 365, when the spring clamp 310 is relaxed, can be varied. In this manner, work pieces of various sizes can be gripped and the gripping force can be varied by changing the spacing between jaw face 322 and pad 365.

Furthermore, it may be desirable to provide a jaw nut 366 on thumb screw 363. By tightening jaw nut 366 against longitudinal arm 362, thumb screw 363 will be prevented from rotating, and therefore, the size of the spacing between jaw face 322 and pad 365 can be maintained throughout successive clamping operations.

Thus, in view of the foregoing disclosure, it should be evident that a spring clamp embodying the concept of the invention disclosed herein carries out the various objects of the invention and otherwise constitutes an advantageous contribution to the art.

I claim:

1. A spring clamp, comprising:
   a first body member having a jaw end and a handle end having an inwardly facing surface with a rib extending longitudinally substantially along said surface;
   a second body member having a jaw end and a handle end having an inwardly facing surface with a rib extending longitudinally substantially along said surface;
   a bridging member integral with said first body member and said second body member, and interposed between said jaw end and said handle end of each said body member;
   spring means interposed between said respective handle ends and engaging each said handle end; and
   means to retain said spring means in engagement with each said handle end;
   said spring means having a corresponding groove engageable with said rib when said spring means is interposed between said respective handle ends.

2. A spring clamp according to claim 1 wherein said spring means has an outer surface, said groove extending longitudinally along said outer surface.

3. A spring clamp according to claim 1 wherein said means to retain comprises a retaining wall integral with said handle end of a said body member and a corresponding end wall on said spring means engageable with said end wall when said spring means is interposed between said respective handle ends.

4. A spring clamp according to claim 3 wherein said bridging member has an arcuate wall presented toward said handle ends.

5. A spring clamp according to claim 4 wherein each said handle end has an inwardly facing surface intersecting said arcuate wall.

6. A spring clamp according to claim 5 wherein said spring means has an outer surface engageable with said inwardly facing surface substantially along the length of said inwardly facing surface.

7. A spring clamp according to claim 6 wherein said outer surface of said spring means engages a portion of said arcuate wall when the spring clamp is in an unflexed condition.

8. A spring clamp according to claim 1 wherein said jaw ends have at least one set of complementary jaw teeth.

9. A spring clamp according to claim 1 wherein at least one of said jaw ends presents a C-shaped configuration.

10. A spring clamp according to claim 9 wherein said other jaw end presents a C-shaped configuration in opposition to said one jaw end.

11. A spring clamp according to claim 9 wherein said other jaw end includes adjustable screw means having a pad presented in opposition to said one jaw end.

12. A spring clamp according to claim 1 wherein said body members and said bridging member are one-piece molded non-metallic material.

13. A spring clamp according to claim 12 wherein said material is nylon.

14. A spring clamp according to claim 13 wherein said spring means is molded of non-metallic material.

15. A spring clamp according to claim 14 wherein said spring means is nylon.

* * * * *